(12) United States Patent
Bau-Madsen et al.

(10) Patent No.: US 10,307,754 B2
(45) Date of Patent: Jun. 4, 2019

(54) MICROFLUIDIC DETECTION SYSTEM AND A MICROFLUIDIC CARTRIDGE

(71) Applicant: SCANDINAVIAN MICRO BIODEVICES APS, Farum (DK)

(72) Inventors: Niels Kristian Bau-Madsen, Hellerup (DK); Lars Bue Nielsen, København S (DK); Martin Heller, Gentofte (DK); Ole Kring, Birkerød (DK); Olga Ordeig, København K (DK); Bent Overby, Glostrup (DK)

(73) Assignee: SCANDINAVIAN MICRO BIODEVICES APS, Farum (DK)

( * ) Notice: Subject to any disclaimer, the term of this patent is extended or adjusted under 35 U.S.C. 154(b) by 0 days.

(21) Appl. No.: 15/319,542

(22) PCT Filed: Jun. 15, 2015

(86) PCT No.: PCT/DK2015/050166
§ 371 (c)(1),
(2) Date: Dec. 16, 2016

(87) PCT Pub. No.: WO2015/192855
PCT Pub. Date: Dec. 23, 2015

(65) Prior Publication Data
US 2017/0203295 A1 Jul. 20, 2017

(30) Foreign Application Priority Data

Jun. 18, 2014 (DK) .................................. 2014 70363

(51) Int. Cl.
B01L 3/00 (2006.01)
B01L 9/00 (2006.01)
(Continued)

(52) U.S. Cl.
CPC ......... B01L 3/502715 (2013.01); B01L 9/527 (2013.01); G01N 21/05 (2013.01);
(Continued)

(58) Field of Classification Search
CPC ............... B01L 3/502715; B01L 9/527; B01L 2300/02; B01L 2300/0864;
(Continued)

(56) References Cited

U.S. PATENT DOCUMENTS 3,910,701 A  10/1975 Henderson et al.
5,304,487 A   4/1994 Wilding et al.
(Continued)

FOREIGN PATENT DOCUMENTS

WO    WO 93/22053 A1    11/1993
WO    2006/120656 A1    11/2006
(Continued)

OTHER PUBLICATIONS

International Search Report (PCT/ISA/210) dated Sep. 3, 2015, by the Nordic Patent Institute as the International Searching Authority for International Application No. PCT/DK2015/050166.
(Continued)

Primary Examiner — Samuel P Siefke
(74) Attorney, Agent, or Firm — Buchanan Ingersoll & Rooney P.C.

(57) ABSTRACT

A microfluidic cartridge includes first and second sides and at least one flow channel and an inlet to the flow channel(s) for feeding a liquid sample, the flow channel(s) include a plurality of first optical detection sites. A detector assembly includes a slot for inserting the microfluidic cartridge and a first fixed light source with a beam path and an optical reader for reading out optical signals from at least one of the first optical detection site(s). When the microfluidic cartridge is inserted to a first predetermined position into the slot, one of
(Continued)

the first optical detection sites of the microfluidic cartridge is positioned in the beam path of the first light source, and when the cartridge is inserted to a second predetermined position into the slot, another one of the first optical detection sites of the microfluidic cartridge is positioned in the beam path of the first light source.

19 Claims, 9 Drawing Sheets

(51) Int. Cl.
*G01N 21/05* (2006.01)
*G01N 21/31* (2006.01)
*G01N 21/64* (2006.01)
*G01N 35/00* (2006.01)
*G01N 21/25* (2006.01)
*G01N 27/403* (2006.01)
*G01N 21/03* (2006.01)

(52) U.S. Cl.
CPC .......... *G01N 21/25* (2013.01); *G01N 21/255* (2013.01); *G01N 21/31* (2013.01); *G01N 21/6428* (2013.01); *G01N 27/403* (2013.01); *G01N 35/00029* (2013.01); *G01N 35/00732* (2013.01); *B01L 2200/025* (2013.01); *B01L 2300/02* (2013.01); *B01L 2300/0645* (2013.01); *B01L 2300/0654* (2013.01); *B01L 2300/0816* (2013.01); *B01L 2300/0864* (2013.01); *G01N 2021/0346* (2013.01); *G01N 2021/6439* (2013.01); *G01N 2035/00237* (2013.01); *G01N 2035/00752* (2013.01); *G01N 2035/00811* (2013.01); *G01N 2035/00851* (2013.01); *G01N 2201/062* (2013.01); *G01N 2201/0627* (2013.01)

(58) Field of Classification Search
CPC ..... B01L 2300/0816; B01L 2300/0654; B01L 2300/0645; B01L 2200/025; G01N 21/255; G01N 27/403; G01N 35/00732; G01N 21/25; G01N 35/00029; G01N 21/05; G01N 21/6428; G01N 21/31; G01N 2035/00811; G01N 2201/0627; G01N 2201/062; G01N 2035/00237; G01N 2035/00752; G01N 2035/00851; G01N 2021/0346; G01N 2021/6439
See application file for complete search history.

(56) References Cited

U.S. PATENT DOCUMENTS

| | | |
|---|---|---|
| 7,498,177 B2 | 3/2009 | De La Fuente et al. |
| 7,791,728 B2 | 9/2010 | Beatty et al. |
| 2003/0116436 A1 | 6/2003 | Amirkhanian et al. |
| 2004/0101443 A1 | 5/2004 | Kagan et al. |
| 2005/0243304 A1 | 11/2005 | Padmanabhan et al. |
| 2006/0063160 A1 | 3/2006 | West et al. |
| 2006/0160205 A1* | 7/2006 | Blackburn .......... B01F 13/0059 435/287.2 |
| 2007/0129650 A1 | 6/2007 | Freeman et al. |
| 2007/0166196 A1 | 7/2007 | Bardell et al. |
| 2007/0286774 A1 | 12/2007 | Barholm-Hansen et al. |
| 2009/0317793 A1 | 12/2009 | Jonsmann et al. |
| 2010/0029011 A1 | 2/2010 | Sin |
| 2011/0045492 A1 | 2/2011 | Bau-Madsen et al. |
| 2011/0253224 A1 | 10/2011 | Linder et al. |
| 2011/0256551 A1 | 10/2011 | Linder et al. |
| 2012/0035061 A1 | 2/2012 | Bransky et al. |
| 2012/0115214 A1 | 5/2012 | Battrell et al. |
| 2013/0027695 A1 | 1/2013 | Salsman |
| 2013/0309778 A1 | 11/2013 | Lowe et al. |
| 2015/0247845 A1 | 9/2015 | Heller et al. |

FOREIGN PATENT DOCUMENTS

| | | |
|---|---|---|
| WO | WO 2007/075922 A2 | 7/2007 |
| WO | WO 2010/088514 A1 | 8/2010 |
| WO | WO 2011/130629 A1 | 10/2011 |
| WO | WO 2012/016107 A1 | 2/2012 |
| WO | WO 2012/032294 A1 | 3/2012 |
| WO | WO 2013/189502 A1 | 12/2013 |

OTHER PUBLICATIONS

Written Opinion (PCT/ISA/237) dated Sep. 3, 2015, by the Nordic Patent Institute as the International Searching Authority for International Application No. PCT/DK2015/050166.

International Preliminary Report on Patentability (PCT/IB/373) dated Dec. 20, 2016, by the International Bureau of WIPO as the International Searching Authority for International Application No. PCT/DK2015/050166.

Danish Search Report dated Jan. 14, 2015, by the Danish Patent and Trademark Office as the Search Authority for Danish Patent Application No. PA 2014-70363.

Danish Search Opinion dated Jan. 14, 2015, by the Danish Patent and Trademark Office as the Search Authority for Danish Patent Application No. PA 2014-70363.

Ruckstuhl et al., Supercritical angle fluorescence (SAF) microscopy, Optics Express, 2004, pp. 4246-4254, vol. 12, Issue 18.

Partial Supplementary European Search Report dated Jan. 12, 2018, by the European Patent Office in corresponding European Application No. 15810324.2-1020. (26 pages).

* cited by examiner

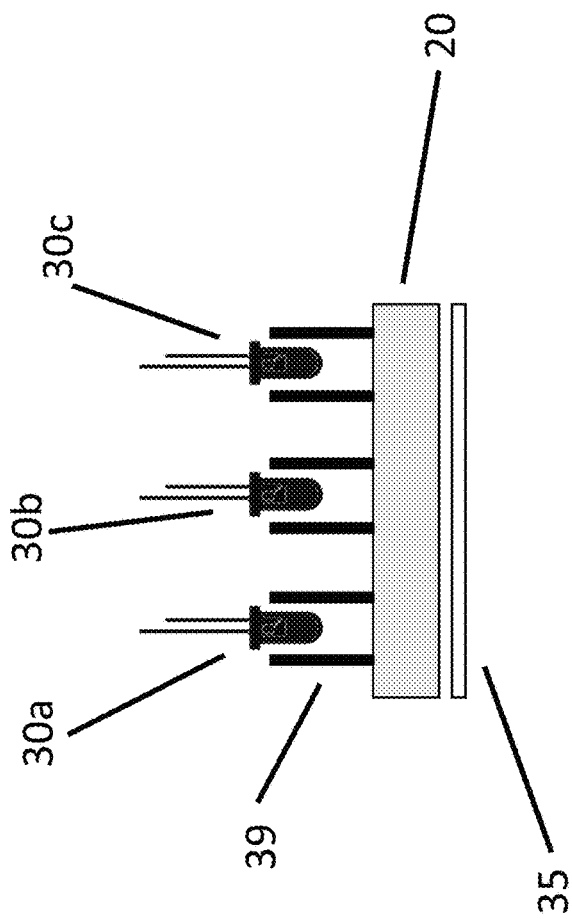

MICROFLUIDIC DETECTION SYSTEM AND A MICROFLUIDIC CARTRIDGE

TECHNICAL FIELD

The invention relates to a microfluidic detection system suitable for performing optical assays of a sample and a microfluidic cartridge suitable for such microfluidic detection system.

BACKGROUND ART

Microfluidic detection systems and microfluidic cartridges of such systems are well known in the art. Such microfluidic detection system usually comprises a detector assembly and at least one microfluidic cartridge, where the microfluidic cartridge is shaped to hold a sample e.g. a liquid sample in a flow channel of the microfluidic cartridge. The microfluidic cartridge can be inserted into a slot of the detector assembly for optical analyses. Such microfluidic detection systems are usually used for performing analysis of liquids very fast and at relatively low cost. Often such microfluidic detection systems are used for high through put analysis. Due to development of standard analyses which can be performed at the doctor or even at a home of a patient, it is required that the general cost for the microfluidic detection system is relatively low.

Many of the standard analysis require that the sample should be subjected to several tests using optical light sources having different wavelengths.

U.S. Pat. No. 3,910,701 discloses an apparatus for measuring light reflectance, absorption and/or transmission having a plurality of light emitting diodes (LEDs) arranged to direct light emissions toward a test piece, with the various diodes being selected to emit light of different wavelengths and at least one light-responsive sensor disposed to receive light reflected and/or transmitted by the test piece and originating with each of the light-emitting diodes. Electrical drive circuit means are provided for alternately or sequentially energizing the plurality of LEDs of different wavelengths, such that the reflected or transmitted light received by the sensor is a function of the various wavelengths of the respective LEDs. The plurality of LED sources and the light responsive sensor are mounted within a self-contained module, of size and shape similar to a camera lens, and the module is detachably connected to a portable housing for the instrument. In this manner, a number of different source modules may be provided for each detection site simply by moving the module.

U.S. Pat. No. 7,791,728 discloses a microfluidic analysis system for optically analyzing a substance that includes a light source having a plurality of selectable single-wavelength light sources, a substance presentation member optically coupled to the light source, and an optical detection system associated with the substance presentation member. The light source and wavelength selection system include a light generating carousel having a plurality of single-wavelength light sources coupled thereto. The carousel can be rotated for position of the desired single-wavelength light source for a test. The microfluidic analysis system is suitable for completing an optical analysis on a millimeter or microliter scale volume of fluid due to the use of the multi-wavelength selector structure having multiple single-wavelength light sources such as light emitting diodes (LEDs) or lasers.

DISCLOSURE OF INVENTION

An object of the invention is to provide a microfluidic detection system which can be applied for performing a plurality of analysis in a very fast and simple manner.

An object of the invention is to provide a microfluidic detection system which can be applied for performing analysis of very high accuracy at a relatively low cost.

A further object of the invention is to provide a microfluidic detection system which is stable and has a long durability.

In an embodiment it is an object of the invention to provide a microfluidic cartridge which is suitable for performing a plurality of different assays and which microfluidic cartridge advantageously can be applied as a part of the microfluidic detection system.

In an embodiment it is an to provide a microfluidic detection system which can be applied for performing analysis on very small liquid samples, such a samples of body fluids, where the microfluidic detection system can be applied for a plurality of different assays involving use of light beams of different wavelengths while simultaneously the cost of the microfluidic detection system is relatively low.

These and other objects have been solved by the invention as defined in the claims and as described herein below.

It has been found that the invention and embodiments thereof have a number of additional advantages which will be clear to the skilled person from the following description.

The microfluidic detection system of the invention is a very compact system which can be applied in a wide range of different analysis and where only minor amounts of liquid sample are required for each analysis. The test can be performed in a very fast way and accordingly the microfluidic detection system may be applied for high throughput analysis.

The terms "test" and "analysis" are used interchangeably.

The microfluidic detection system of the invention comprises a microfluidic cartridge and a detector assembly.

The microfluidic cartridge can in principle be any microfluidic cartridge suitable of optical read out. The microfluidic cartridge comprises a first and a second side and at least one flow channel and at least one inlet to the one or more flow channels for feeding a liquid sample. The flow channel or flow channels comprises a plurality of first optical detection sites.

Example of suitable microfluidic cartridges are for example those microfluidic cartridges described in WO13189502, US2011045492, US2009317793 or US2007286774 optionally modified to have a plurality of detection sites. Further preferred microfluidic cartridges are described below.

The detector assembly comprises a slot for inserting the microfluidic cartridge and a first fixed light source with a beam path and an optical reader for reading out optical signals from the first optical detection site. The slot of the detector is shaped such that when the microfluidic cartridge is inserted into the slot, at least one of the first optical detection sites of the microfluidic cartridge is positioned in the beam path of the first light source. In an embodiment the first light source comprises a multicolor light emitting diode (LED) configured for emitting a plurality of different light beams having different wavelengths and a circuitry for switching the plurality of different light beams on and off. Advantageously the different light beams preferably have a narrow spectral width. This will be discussed further below.

The term "fixed light source" means a light source that is operable only in one physical position within the detector assembly. In use the fixed light source is in this single operable position. The light source may advantageously be replaced when broken or for other reasons inoperable by dismounting the inoperable light source with a replacement light source.

The fact that the light source is a fixed light source and not a movable light source makes the microfluidic detection system very compact while it simultaneously is very stable and/or robust compared to prior art microfluidic detection systems.

The term "beam path" means a path of light. The beam path may be manipulated e.g. by one or more lenses or mirrors or other optical components. Advantageously at least a part of the beam path is in free space between the LED and the optical detection site positioned in the beam path.

In an embodiment the LED is arranged to directly illuminate one of said first detection sites without use of additional optical element(s) i.e. without any optical components arranged in the one or more beam paths.

The term "optical detection site" means a part of one of the one or more flow channels of the microfluidic cartridge with a transparent window and comprising or constructed to comprise a sample part subjected to the optical analysis via the transparent window. An optical detection site is advantageously a relatively small part of the at least one flow channel, preferably in the form of section of the at least one flow channel and/or a chamber preferably in fluid connection to at least one of the at least one flow channel.

The optical detection site may be determined as the site irradiated by the light beams and from which the signals are directed to the optical reader.

The term "optical detection site" may be at least one of the first optical detection site.

The term "optical detection site" used in singular should also be interpreted to include the plural form of the "optical detection sites", unless otherwise specified.

The term "first optical detection site" is meant to denote optical detection site(s) which is to be illuminated from the first fixed light source.

The term "light beam" is herein used to mean a directional projection of light emitted from the Led. The light beams are not continuous but may have a desired duration sufficient to perform the desired analysis. A suitable duration may e.g. be up to 10 seconds, such as from about 1 ms to about 5 seconds.

The term "rays of light" is used to denote a part of the light beam i.e. the light beam comprises a plurality of rays.

The slot in the detector assembly is adapted to the microfluidic cartridge. Normally the microfluidic detection system will comprise a plurality of microfluidic cartridges which one after the other may be inserted into the detector assembly for performing at least one analysis.

The slot in the detector assembly may in an embodiment be adapted to microfluidic cartridges of different shapes and/or sizes.

In an embodiment the slot of the detector assembly and the microfluidic cartridge are constructed such that when the microfluidic cartridge is inserted fully into the slot, at least one of the first detection sites of the microfluidic cartridge is positioned in the beam path of the first light source. Thereby it is simple to insert the microfluidic cartridge and position the optical detection site correctly within the detector assembly.

The slot of the detector assembly and the microfluidic cartridge are constructed such that when the microfluidic cartridge is inserted to a predetermined position into the slot, at least one of the first detection sites of the microfluidic cartridge is positioned in the beam path of the first light source. The microfluidic cartridge need not be fully inserted. The predetermined position of the microfluidic cartridge into the slot is determined by a click arrangement holding the microfluidic cartridge in a temporally fixed position. Thereby the microfluidic cartridge may have several optical detection sites which one after the other can be positioned within the detector assembly to be in the beam path of a light source e.g. the same light source.

Such click arrangements are well known and may comprise projecting flanges and/or cavities on the microfluidic cartridge and/or the detector assembly at selected positions which engage or snap into place to position the microfluidic cartridge in the detector assembly.

In an embodiment the detector assembly is arranged to position the microfluidic cartridge in one or more desired positions. Such automatic or semi-automatic handling of microfluidic cartridges is well known in other prior art systems.

The optical detection site has a transparent window for the at least two different light beams. The transparent window is for example in the form of a transparent wall section of the at least one flow channel.

The microfluidic cartridge may advantageously be at least partly of transparent glass or polymer. In a preferred embodiment the microfluidic cartridge comprises a polymer substrate having one or more channel shaped cavities which are covered by a foil which in at least the optical detection site is transparent to thereby form the flow channel or flow channels.

In an embodiment the cartridge comprises one or more integrated lenses and/or mirrors arranged in or adjacent the optical detection site. The one or more integrated lenses and/or mirrors may act to direct, and/or focus the beams to the optical detection site.

One or more integrated lenses and/or mirrors and/or other optical components may be arranged at any desired position in the microfluidic detection system in order to guide the beams, to direct the beams, to confine the beams, to focus the beams and/or to collimate the beams or in other ways manipulate the beams.

At least one of the first detection sites has a transparent window for reading out optical signals from the optical detection site. In an embodiment at least one of the first detection sites has a transparent window for the at least two different light beams and for reading out optical signals.

As described below in further detail it may be advantageous to provide the microfluidic cartridge from a substrate with cavities and/or channels and a cover for the substrate and optionally other elements such as electrical transmissions lines, anodes, cathodes and/or other components, where at least one of the substrate and the cover is of a transparent material to thereby provide the transparent window.

In an embodiment the LED and the optical reader are positioned on opposite sides of the microfluidic cartridge when the cartridge is inserted into the slot of the detector assembly. The LED is arranged to direct the beams towards the optical detection site and the optical reader is arranged to read signals in the form of not absorbed or reflected light i.e. the light that passes through the optical detection site. In this arrangement the optical reader may also be arranged to read signals emitted light from excited fluorophores.

Preferably the LED and the optical reader are positioned on the same side of the microfluidic cartridge when the cartridge is inserted into the slot of the detector assembly. The LED is arranged to direct the beams towards the optical detection site and the optical reader is arranged to read signals in the form of reflected light signals or signals emitted light from excited fluorophores.

In an embodiment the optical reader is positioned to collect signals in the form of light exceeding the critical angle of total internal reflection. Such construction is particularly advantageous for performing supercritical angle fluorescence (SAF) assays where the target to be determined is marked with fluorophores. By using SAF a very high resolution can be obtained in a simple and effective way. SAF methods have in the prior art preliminarily been used in simple microscopy such as described in Supercritical angle fluorescence (SAF) microscopy, by Thomas Ruckstuhl and Dorinel Verdes, Optics Express, Vol. 12, Issue 18, pp. 4246-4254 (2004). These SAF structures and methods can in a simple way be modified to be applied in the microfluidic detection system of the present invention.

The SAF method and structure is particularly useful for performing immune assays.

In an embodiment the optical reader is arranged for reading out at least one absorption property from a liquid sample in at least one of the first detection sites when the cartridge is inserted into the slot of the detector assembly.

In an embodiment the optical reader is arranged for reading out at least one reflection property from a liquid sample in at least one of the first detection sites when the cartridge is inserted into the slot of the detector assembly.

In an embodiment the optical reader is arranged for reading out at least one emitting property from a liquid sample in at least one of the first detection sites when the cartridge is inserted into the slot of the detector assembly.

The optical reader can in principle be any kind of photo detector capable of sensing the wavelength in question, i.e. light rays with the wavelength which is expected to be obtained from the optical detection site e.g. emitted or reflected or passing through the optical detection site Advantageously the optical reader is a multiple wavelength reader.

In an embodiment the reader comprises a photodiode array and/or a photomultiplier tubes. Suitable detectors may e.g. be acquired from Hamamatsu Cooperation, Bridgewater, US or from Atmel Corporation, San Jose, US.

In an embodiment the optical reader is a digital imaging reader, preferably in the form of a charge-coupled device (CCD) reader.

Advantageously the CCD reader is a color reader, such as a 3CCD reader or a color filter mosaic CCD reader.

A 3CCD reader is a CCD reader comprising a dichroic beam splitter prism that splits the image into red, green and blue components.

A color filter mosaic CCD reader is a CCD reader comprising a color filter such as a Bayer mask, a RGBW mask (Red, Green, Blue, White filter array), or a CYGM mask (Cyan, Yellow, Green, Magenta filter array).

Advantageously the optical reader is a spectrometer, the spectrometer is preferably configured to operate with a band width comprising the at least two different light beams.

A spectrometer is also often called a spectroscope and is used to measure properties, such as intensity or polarization of light over a specific band width.

Preferably the spectrometer is configured to determine the intensities of light over a band width comprising visible light.

In an embodiment the spectrometer is configured to determine the intensities of light over a band width comprising at least two different light beams.

In an embodiment the spectrometer is configured to determine the intensities of light over a band width of at least about 20 nm, preferably at least over a band width of at least about 100 nm, such as up to 800 nm. In an embodiment the spectrometer has a spectral resolution of from about 0.5 to about 20 nm, such as from about 5 to about 1 nm.

In an embodiment the optical reader is a fiber-optic spectrometer comprising a plurality of optical fibres arranged to receive rays of the light from the optical detection site. The fiber-optic spectrometer may for example be arranged such that the respective fibers are bundled in one end thereof and are arranged to collect rays of the light from the optical detection site and in another end of the fibers the fiber bundle is split into two or more single fibers or sub-bundles of fibers, each second-end single fiber or sub-bundle being connected to a spectrometer for analyzing of light within respective preselected wavelength ranges.

The spectrometer may comprise a CCD reader.

In an embodiment the circuitry of the first light source is configured for switching the plurality of different light beams on and off independently of each other, preferably the detector assembly is programmed to control the circuitry of the first light source.

The LED is advantageously constructed such that only one light beam is emitted at a time and such that the plurality of different light beams can be switched on and off one after the other. The duration of the respective light beams may be equal or different and advantageously the duration is a few seconds such as up to 10 seconds.

In an embodiment the detector assembly is programmed to switch the plurality of different light beams on and off one at a time, in a predetermined pattern, the predetermined pattern is advantageously selected depending on the detection assay to be performed.

In an embodiment the detector assembly is programmed to switch the plurality of different light beams on and off such that only one of the different light beams of the LED is switched on at a time.

In an embodiment the plurality of different light beams comprises at least two different light beams, such as from 2 to 5 different light beams.

Generally it is desired that the light beams each have a narrow spectral width, preferably of 100 nm or less. Preferably the different light beams independently of each other have a spectral width of up to about 50 nm. By using light beams with such narrow spectral width the microfluidic detection system can be applied to detect different components and/or components marked with different fluorophores with a high resolution even where concentrations are very small or very large and furthermore the determination may be both qualitative and quantitative.

The term 'bandwidth' is herein used to mean 'wavelength bandwidth'.

The term 'spectral width' is herein used to mean the range of wavelengths of a light beam emitted from the light source and surrounding a center wavelength at a power level equal to half the maximum power level.

In an embodiment each of the plurality of different light beams of the multicolor-LED independently of each other have a spectral width of up to about 25 nm.

In an embodiment each of the plurality of different light beams multicolor-LED independently of each other have a spectral width of up to about 5 nm.

In an embodiment each of the plurality of different light beams multicolor-LED independently of each other have a spectral width of up to about 2 nm.

Advantageously the plurality of different light beams of the multicolor-LED are monochromatic light beams.

In principle the multicolor-LED may comprise light beam having any center wavelength and/or peak wave length, preferably adapted to the target to be analyzed.

The center wavelength and peak wave length of the respective light beams may be equal or differ from each other. For optional analysis the microfluidic detection system may be calibrated prior to performing the assay in order to exclude systemic errors or to account for drift or temperature variations.

In an embodiment the plurality of different light beams of the multicolor-LED comprise a light beam having a center wavelength of about 575 nm to about 625 nm.

In an embodiment the plurality of different light beams of the multicolor-LED comprise a light beam having a center wavelength of about 425 nm to about 475 nm, preferable about 450 nm.

In an embodiment the plurality of different light beams of the multicolor-LED comprises a red light beam and a blue light beam.

In an embodiment the multicolor-LED comprises the following light beams.
Red: $610<\lambda<760$.
Orange: $590<\lambda<610$.
Yellow: $570<\lambda<590$.
Green: $500<\lambda<570$.
Blue: $450<\lambda<500$.

In an embodiment the plurality of different light beams of the multicolor-LED comprise at least three monochromatic light beams, selected from red, orange, yellow, green or blue light beams.

Examples of suitable multicolor-LEDS are the Bi-color LEDs (two chips) and Multi-color LEDs (multiple chips) marketed by Marubeni America Corporation, http://tech-led.com/LED_die_bare_chips.shtml.

The multicolor-LED is advantageously amplified e.g. by comprising an integrated amplifier or by a separate amplifier or amplification structure.

In an embodiment the beams from the LED are confined along the beam path to narrow the spot size preferably such that the spot size at at least one of the first detection sites has a desired narrow spot size and a desired high intensity.

Advantageously the microfluidic cartridge has a plurality of optical detection sites.

In an embodiment the flow channel or flow channels of the microfluidic cartridge comprises a plurality of first optical detection sites, the detector assembly and the microfluidic cartridge are constructed such that when the microfluidic cartridge is inserted at a first predetermined position into the slot, one of the first optical detection sites of the microfluidic cartridge is positioned in the beam path of the first light source, and when the cartridge is inserted at a second predetermined position into the slot another one of the first optical detection sites of the microfluidic cartridge is positioned in the beam path of the first light source, wherein each of the first and the second predetermined positions of the microfluidic cartridge into the slot preferably is determined by a click arrangement holding the microfluidic cartridge in a temporally fixed position.

The click arrangement may be as described above.

Advantageously the microfluidic detection system comprises a plurality of fixed light sources which may be equal or different from each other.

The microfluidic detection system according to the invention also comprises an embodiment in which the flow channel or flow channels of the microfluidic cartridge comprises at least a second optical detection site, and the detector assembly comprises at least a second fixed light source with a beam path, the slot of the detector is shaped such that when the microfluidic cartridge is inserted into the slot, the second optical detection site of the microfluidic cartridge is positioned in the beam path of the second light source, the second light source preferably comprises a multicolor light emitting diode (LED) configured for emitting a plurality of different light beams having different wavelengths and a circuitry for switching the plurality of different light beams on and off.

Advantageously the optical reader which is arranged for reading signal from the first optical detection site(s) is configured for reading out optical signals from the second optical detection site(s).

The terms "arranged for" and "configured for" are used interchangeably.

In an embodiment the detector assembly comprises a second optical reader configured for reading out optical signals from the second optical detection site(s).

Advantageously the flow channel or flow channels of the microfluidic cartridge comprises a plurality of additional optical detection sites, and the detector assembly comprises a plurality of additional fixed light sources with respective beam paths. The slot of the detector is shaped such that when the microfluidic cartridge is inserted into the slot, the plurality of additional optical detection sites of the microfluidic cartridge is positioned in respective the beam paths of the plurality of additional light sources. Each of the plurality of additional light sources preferably comprise a multicolor light emitting diode (LED) configured for emitting a plurality of different light beams having different wavelengths and a circuitry for switching the plurality of different light beams on and off. Thereby a plurality of assays can be performed simultaneously.

The detector assembly may comprise one or a plurality of equal or different readers for reading signals from the plurality of optical detection sites.

In order to avoid or reduce the risk of cross talk between light beams emitted from different LEDs or between signals from different optical detection sites, e.g. due to incident light, the microfluidic detection system may advantageously comprise light guides. The light guide may preferably be arranged to confine the light beam and/or the signals. Optionally the microfluidic detection system may comprise collimating components for further guide the light beams. Lenses and mirrors may in an embodiment be applied to focus and/or directing the light.

In an embodiment the detector assembly comprises a light tunnel for one or more of the fixed light sources to prevent the beams from the respective fixed light sources from transmitting light to two or more detection sites simultaneously. Preferably the light tunnel is structured to avoid transmission of incident light from a fixed light source to a detection site not arranged in the beam path of the light source.

In an embodiment the flow channel or flow channels of the microfluidic cartridge comprises a plurality of detection sites configured for performing a plurality of different assays. The detection sites may comprise any type of detection sites e.g. as described below.

The plurality of detection cites may advantageously comprise at least one electrical detection site. An electrical detection site is a site in the flow channel(s) configured for reading out an electrical signal via electrodes. Therefore the electrical detection site need not be transparent.

The electrical detection site comprises electrodes arranged for performing an electrochemical detection at the electrical detection site. The electrodes comprise electrical wires connected to microfluidic cartridge connection pads.

The electrical wires can be in the form of any type of electrical transmission lines, such as printed metal lines. Other preferences are described below.

The connection pads of the microfluidic cartridge are configured for providing read out electric contact to the detector assembly.

The detector assembly comprises at least one electrical reader for reading out electrical signals out from the electrical detection site(s) via said connection pads.

In an embodiment the electrical reader comprises a voltmeter electrically connected to voltmeter connection pads arranged in the slit such that when the microfluidic cartridge is inserted into the slot the microfluidic cartridge connection pads are in electrical connection with the voltmeter connection pads. Thereby the microfluidic cartridge can in a simple way be accurately positioned relative to the detector assembly e.g. further making use of the click arrangement described above.

Advantageously the detector assembly further comprises at least one output interface such as a display and/or a printer and a processor. The processor may be any kind of processor preferably a programmable computer which is integrated into the detector assembly. In an embodiment the detector assembly is connected to a computer via a wire or via wireless connection.

The detector assembly may for example be connected to a central database comprising patient journals, and by identifying the patient e.g. by scanning a barcode or a chip related to the patient e.g. a bar code on a wrist on the patient or a chip in the patient ensuring that the result is entered into the patient journals in the central database or the detector assembly may receive instructions from the patient journal concerning which assays are to be performed on the sample from the patient.

The processor may be programmed with software for performing one or more desired assays.

In an embodiment the detector assembly is programmed to perform a multiplexing of the read out signals.

In an embodiment the microfluidic cartridge comprises a machine readable code comprising instructions about assays to be performed using the cartridge and the detector assembly comprises a code reader for reading the machine readable code and feeding the instructions about the assays to be performed to the processor, wherein the processor is programmed to control at least one of the reader(s) and the output interface at least partly based on instructions obtained from the machine readable code, preferably the at least one reader is at least one of the optical reader and the electrical reader.

The bar code may be any kind of bar code such as a 1D, a 2D or a 3D bar code.

In an embodiment the detector assembly comprises a plurality of microfluidic cartridges comprising different bar codes coding for different assays.

Advantageously the respective bar codes of the microfluidic cartridges each code for performing read out of a predetermined number of the detection sites.

The bar code system may for example be used to indicate which assays a client should have access to and/or which dispatch sites a client should access to read out from.

Thereby microfluidic cartridges prepared for several different assays could be sold with different bar codes, where respective barcodes codes for allowing use of respective assays. Thereby it is not required to make different microfluidic cartridges for different assays or assay combinations and mass production of one or a few types of microfluidic cartridges for a plurality of different assays instead of making many different types of microfluidic cartridge reduces cost significantly.

In an embodiment at least one of the microfluidic cartridges comprises a bar code coding for performing read outs from only some of the detection sites.

The detector assembly is advantageously programmed using suitable software. The software advantageously comprises a central database which can be used in analyzing the resulting detection e.g. for calibration against tests performed on samples with known compositions.

In an embodiment the software comprises a database having data identifying preselected diseases and if a patient has one of these diseases it can be identified when performing assays on a sample from this patients. Thereby outbreaks of infectious diseases for example in a region can relatively fast be identified.

In an embodiment the software comprises a database having data identifying preselected pathogen components, such as pathogen microorganisms for which an assay can be performed, by performing the assay the concentration of such pathogen components in a sample from a patient can be determined very fast, and during treatment of the patient monitoring of treatment progress compared to other similar patients can be performed.

In an embodiment the software comprises a program for performing built-in decision-tree for multiple assay results thereby providing an adaptive response depending on actual number of assays run on a sample.

In an embodiment batch information of the microfluidic cartridge is in a central database and the detector assembly can access this information via the barcode or via a batch number. Thereby limited data on the microfluidic cartridge are required.

The detector assembly may preferably comprise a temperature controlling element arranged to be in contact with the microfluidic cartridge in the slot, and preferably adjacent to at least one of the detection sites when the microfluidic cartridge is inserted into the slot of the detector assembly.

Such a temperature controlling element can for example comprise a peltier element, a thin film heating element and/or other resistive heating elements.

In an embodiment the detector assembly is constructed to perform a pumping effect in the flow channel of the microfluidic cartridge by alternately applying heating and cooling air in a pumping chamber of the microfluidic cartridge where the pumping chamber is in fluid contact with the flow channel. By alternately applying heating and cooling air in the pumping chamber, the pressure in the pumping chamber will alternately increase and decrease thereby resulting in a pumping effect.

In an embodiment the detector assembly comprises a movable pin for actuating a liquid sample in the flow channel. The microfluidic cartridge which can be applied in this embodiment comprises a flexible membrane e.g. in the form of a foil, covering a part of the flow channel or a chamber in fluid connection with the flow channel and the pin is arranged to be pressed into the channel or chamber to perform a pumping effect.

Such pumping effect may be applied to fill up desired areas e.g. chambers of the flow channel and/or to perform a mixing of liquids and solids.

In an embodiment the detector assembly comprises an actuator e.g. in the form of a movable pin for temporarily depressing and optionally closing the flow channel.

The actuator is e.g. a step motor driven actuator for example such as described in WO2012016107.

The actuator may form a membrane pump which in combination with hydraulic resistance can ensure filling of one or more chambers, such as all chambers.

In use the liquid sample is fed to the microfluidic cartridge and the microfluidic cartridge is inserted into the slot of the detector assembly e.g. manually or using a robot e.g. a cassette-robot function.

Preferred micro fluidic devices will be described further below.

The term "liquid sample" means any liquid containing sample including liquid sample comprising solid parts, such as dispersions and suspensions. The sample comprises liquid at the time of performing the method.

In principle any liquid sample can be applied, including but not limited to liquid samples comprising particles, such as dispersed particles. In one embodiment the liquid sample is crushed food or tissue optionally blended with water or it may be an extract thereof. Thus, the microfluidic detection system can for example be applied for performing quantitative and/or qualitative tests on tissue, vegetables, meat and etc.

In an embodiment the liquid sample comprises human or animal faeces e.g. in an aqueous suspension.

In an embodiment the liquid sample comprises waste water or water from a nature source e.g. a lake or a river.

In an embodiment the liquid sample comprises markers such a fluorophores preferably bonded to a target component toward which at least one assay is to be performed. The fluorophores may in an embodiment be bonded to a magnetic particle.

Generally it is desired to select fluorophores with a relatively specific emission wavelength and energy for a simpler qualitative or quantitative determination of the target component. In particular it is desired that the emission wavelength is relatively specific, i.e. it should preferably have a wavelength band which in the method of determination is sufficiently narrow to be distinguished from other emissions.

The term "relatively specific wavelength" means that the wavelength can be distinguished from other emitting wavelengths in the test.

In particular in situations where there are several different fluorophores and optionally several target components it is preferred that the fluorophores have relatively specific emission wavelengths such that emission from the respective fluorophores can be distinguished from each other.

The fluorophores can be any type of fluorophores which can be configured to bind to the capture sites of the magnetic particles. Fluorophores are well known to the skilled person and are commercially available.

Examples of quantum dots are described in U.S. Pat. No. 7,498,177 and the quantum dots available from Life Technologies Europe BV. include more than 150 different product configurations with emission wavelength spanning in a broad wavelength range for examples quantum dots with the respective emission wavelengths: 525, 545, 565, 585, 605, 625, 655 and IR 705 and 800 nm. In an embodiment StreptAvidin, Biotin, antibodies and a number of different functionalities have been conjugated in the Invitrogen/life Technologies portfolio of Quantum dot products.

Examples of quantum dots also include quantum dots available from Ocean NanoTech, Springdale, Ark. 72764, including more than 40 different product configurations with emission wavelength spanning in nm and a functionalized outer core of PEG or other biological compatible coating, for example with the respective emission wavelengths: 530, 550, 580, 590, 600, 610, 620 and 630 nm. The quantum dots from Ocean NanoTech include quantum dots with different functional groups e.g. amine, COOH, phenylboronic acid (PBA), as well as quantum dots with amphiphilic polymer and PEG coating. Other examples of quantum dots available from Ocean NanoTech are quantum dots with a sole core e.g. provided in toluene and with only an octadecylamine coat or with amphiphilic polymer and PEG coating.

In an embodiment the fluorophores are quantum dots or aromatic probes and/or conjugated probes, such as fluorescein, derivatives of benzene, metal-chalcogenide fluorophores or combinations thereof.

The fluorophores may in an embodiment be configured to bind to a selected capture sites e.g. within an optical detection site of the microfluidic cartridge.

The invention also relates to a preferred microfluidic cartridge suitable for being a part of the microfluidic detection system. The microfluidic cartridge of the invention can also be used alone or together with prior art detector assemblies.

The microfluidic cartridge of the invention may be as described above.

The microfluidic cartridge of the invention is designed for performing a plurality of different assays. The cartridge comprises at least one flow channel and an inlet to the flow channel(s) for feeding a liquid sample. The flow channel(s) comprises a plurality of detection cites comprising at least one electrical detection site comprising electrodes arranged for performing an electrochemical detection at the electrical detection site, and at least one optical detection site with a transparent window for optical readout at the optical detection site.

Heretofore it has never been suggested to provide a microfluidic cartridge which can be applied for simultaneously performing optical and electrical red outs from the same sample. The microfluidic detection system of the invention thereby provides a new concept which opens up for a new range of combined assays to be performed very fast and on the same sample. This microfluidic cartridge is both time saving and furthermore the results obtained may be more accurate because the electrical and the optical test can be performed at the same time and at the same sample.

Advantageously the cartridge comprises a plurality of electrical detection sites and/or a plurality of optical detection sites.

Preferably each of the one or more optical detection sites is in the form of a chamber having a cross sectional area which is at least about 25%, such as at least about 50%, such as at least 100% larger than a cross sectional area of the flow channel leading to the chamber.

The respective chambers may have equal or different size.

Advantageously one or more of the optical detection sites comprise a reagent, preferably all of the optical detection sites comprise a reaction agent. The reagent can in principle be any reagent, such as the reagents known from prior art.

In an embodiment at least one optical detection site of the cartridge is an absorption optical detection site configured for absorption detection, the absorption optical detection site preferably comprises at least one reagent selected from agglutination reagents, coagulation reagents, an antibody and/or an antigen.

In an embodiment at least one optical detection site of the cartridge is a colorimetric detection site configured for colorimetric detection, preferably the colorimetric detection site comprises at least one reagent selected from color-forming reagents.

The color-forming reagent can be any kind of reagent that induces a color change upon reaction with a target to be tested for using the microfluidic cartridge.

Targets that can be subjects to a colorimetric detection e.g. by being converted chemically to a colored product via a color-producing reaction include enzyme substrates and co-factors. Non-limiting examples of such targets include glucose, cholesterol, and triglycerides. In particular, levels of total cholesterol (i.e., the sum of free and esterified cholesterol) in a body fluid can be spectrophotometrically measured by well-known color-forming assays by reacting the fluid with color-forming reactants including cholesterol esterase, cholesterol oxidase, an oxidizable dye such as n,n-bis(4-sulfobutyl)-3-methylaniline, disodium salt (TODB), 4-aminoantipyrine, and horse radish peroxidase.

A vast number of color-forming reactants may be used for catalyzing the formation of colored products. Examples of such color-forming reactants include alanine aminotransferase (ALT) and aspartate aminotransferase. Alanine aminotransferase (ALT) is a reactant indicative of liver function. Other suitable color-forming reactants include alphaketoglutarate, pyruvate oxidase, an oxidizable dye such as N,N-Bis (4-sulfobutyl)-3-methylaniline, disodium salt (TODB), 4-aminoantipyrine, and horse radish peroxidase.

Other targets which may be detected via a color-producing colorimetric detection comprise targets found by immunoassays, such as an enzyme-linked immunosorbent assay (ELISA). In a typical ELISA, a target is specifically bound by an antibody, which in turn is detected by a secondary, enzyme-linked antibody. The linked enzyme (the color-forming reactants) catalyzes a color-producing reaction. Such enzymes include but are not limited to beta-galactosidase, alkaline phosphatase, and horse radish peroxidase.

The choice of suitable color-forming reactants will depend on the particular target being examined. In general, any color-forming reactants capable of reacting with a target either directly or indirectly to generate colored products is suitable for use in the microfluidic cartridge of the present invention.

In an embodiment at least one optical detection site of the cartridge is a spectroscopic detection site configured for spectroscopic detection, preferably the spectroscopic detection site comprises at least one reagent selected from markers e.g. fluorophores such as the fluorophores described above.

In an embodiment the cartridge comprises a solid substrate with at least one channel shaped cavity for forming the flow channel(s) with chambers for dispatch sites and optionally additional chambers e.g. pumping chamber and a sink section such as described in WO2012016107.

A flexible foil is bonded to the solid substrate to form the flow channel(s). The foil is preferably bonded to the solid substrate by welding.

In an embodiment the foil is a semi permeable foil for capillary venting e.g. evaporation of selected gasses.

In an embodiment the solid substrate is carrying the electrodes for the at least electrical detection site and electrical transmission lines for reading out from the electrodes. The electrodes and electrical transmissions lines may advantageously be printed electrodes on molded base for increased robustness in mass production.

In an embodiment the foil is a polymer carrying the electrodes for the at least electrical detection site and electrical transmission lines for reading out from the electrodes.

In an embodiment electrodes are provided on both sides of the foil, preferably with through holes to ease connectivity and to improve robustness of the electrodes.

Advantageously the electrodes and/or the electrical transmission lines are applied by vapor deposition, sputtering and/or printing, preferably at least one of the electrodes and/or the electrical transmission lines are printed.

The printing can be screen printing, gravure printing or transfer printing.

In an embodiment at least a part of the electrical transmission lines are embedded in the polymer, optionally the foil comprises a cover polymer film laminated onto the at least a part of the electrical transmission lines to thereby embed at least the part of the electrical transmission lines.

The polymer foil may for example comprise a thermoplastic polymer, preferably selected from Polystyrene (PS), Polycarbonate (PC) or polyimide (PI).

The microfluidic cartridge can be produced in any suitable materials, e.g. the materials used for prior art microfluidic cartridges.

The microfluidic cartridge may for example be produced from one or more elements made from polymers, such as polymers selected from cyclic olefin copolymers (COC), acrylonitrile-butadiene-styrene copolymer, polycarbonate, polydimethyl-siloxane (PDMS), polyethylene (PE), polymethylmethacrylate (PMMA), polymethylpentene, polypropylene, polystyrene, polysulfone, polytetra-fluoroethylene (PTFE), polyurethane (PU), polyvinylchloride (PVC), polyvinylidene chloride (PVDC), polyvinylidine fluoride, styrene-acryl copolymers polyisoprene, polybutadiene, polychloroprene, polyisobutylene, poly(styrene-butadiene-styrene), silicones, epoxy resins, Poly ether block amide, polyester, acrylonitrile butadiene styrene (ABS), acrylic, celluloid, cellulose acetate, ethylene-vinyl acetate (EVA), ethylene vinyl alcohol (EVAL), fluoroplastics, polyacetal (POM), polyacrylates (acrylic), polyacrylonitrile (PAN) polyimide (PA), polyimide-imide (PAI), polyaryletherketone (PAEK), polybutadiene (PBD), polybutylene (PB), polybutylene terephthalate (PBT), polyethylene terephthalate (PET), polycyclohexylene dimethylene terephthalate (PCT), polyketone (PK), polyester/polythene/polyethene, polyetheretherketone (PEEK), polyetherimide (PEI), polyethersulfone (PES), polyethylenechlorinates (PEC), polyimide (PI), polylactic acid (PLA), polymethylpentene (PMP), polyphenylene oxide (PPO), polyphenylene sulfide (PPS), polyphthalamide (PPA), and mixtures thereof.

Preferred polymers comprise a polyimide, e.g. a phenylene-pyromellitimide such as poly(4,4'-oxodiphenylene-pyromellitimide e.g. Kapton®.

In an embodiment the microfluidic cartridge is manufactured by providing a rigid substrate comprising one or more channels and optional cavities and/or holes and covering the one or more channels and optional cavities and/or holes with one or more films. The rigid substrate is advantageously produced by injection molding but other molding methods may also be applied. The film may be a polymer or a metal film or a layered film comprising polymer and/or metal e.g. a polymer coated metal film or a metal sputtered polymer film.

At least one of the substrate and the film is transparent to at least one wavelength, preferably within the visible area. Advantageously at least one of the substrate and the film is transparent to at least one of the different light beams of the detector assembly it is supposed to be used together with.

The film may advantageously be welded to the substrate. Gluing may also be provided.

By providing the microfluidic cartridge from a substrate and a film as described the microfluidic cartridge will have a substrate side and a film side.

It should be emphasized that the term "comprises/comprising" when used herein is to be interpreted as an open term, i.e. it should be taken to specify the presence of specifically stated feature(s), such as element(s), unit(s), integer(s), step(s) component(s) and combination(s) thereof, but does not preclude the presence or addition of one or more other stated features.

All features of the inventions including ranges and preferred ranges can be combined in various ways within the scope of the invention, unless there are specific reasons for not to combine such features.

BRIEF DESCRIPTION OF DRAWINGS

The invention will be explained more fully below in connection with a preferred embodiment and with reference to the drawings in which:

FIG. 10 shows a light tunnel, and

The figures are schematic and only intended to show the principles of the invention and may be simplified for clarity. Throughout, the same reference numerals are used for identical or corresponding parts.

Figure 1:
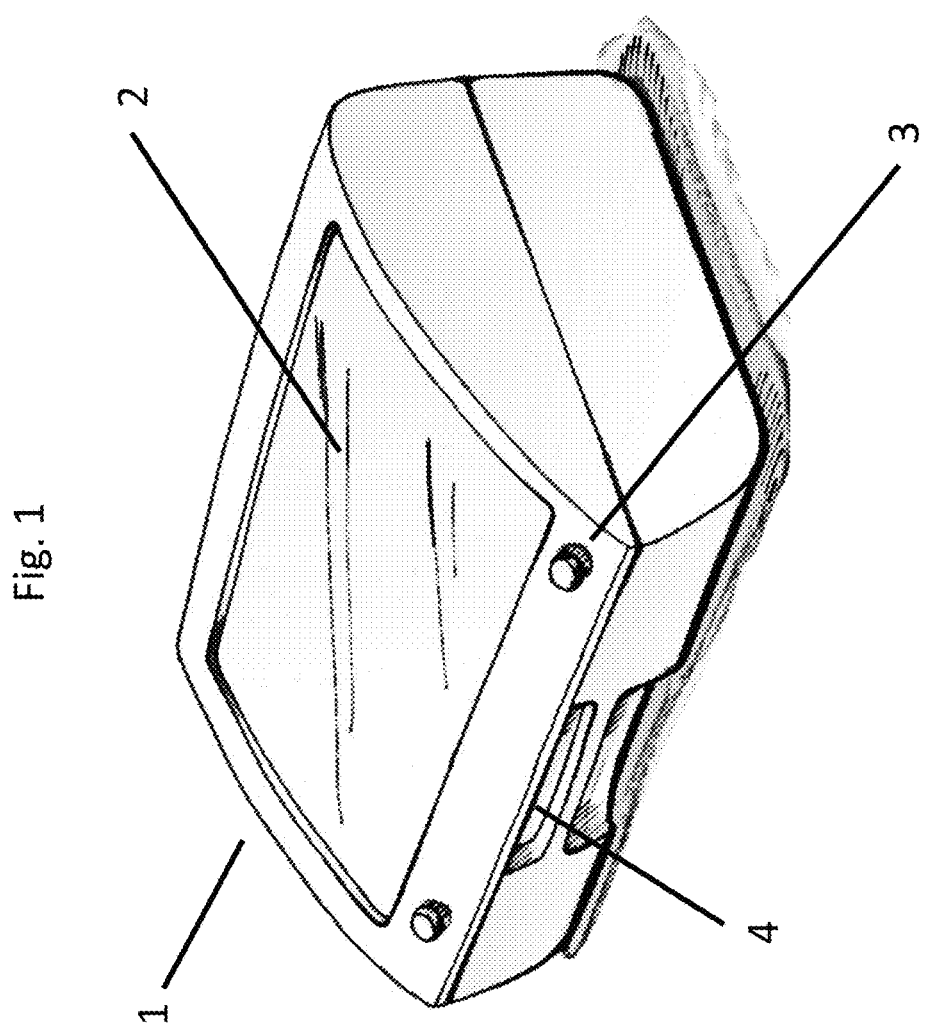
FIG. 1 shows a detector assembly according to the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The invention is defined by the features of the independent claim(s). Preferred embodiments are defined in the dependent claims. Any reference numerals in the claims are intended to be non-limiting for their scope.

Some preferred embodiments have been shown in the foregoing, but it should be stressed that the invention is not limited to these, but may be embodied in other ways within the subject-matter defined in the following claims.

FIG. 1 shows a detector assembly 1 according to the invention. The detector assembly comprises a screen 2, which is used for visually setting the detector assembly and visually display the result of measurements performed on the detector assembly 1.

The detector assembly 1 comprises control buttons 3 which are used for setting and operating the detector assembly. The detector assembly also comprises means for connection with other hardware, such as a computer or printer.

The detector assembly 1 also comprises a slot 4 in which a microfluidic cartridge may be inserted. The microfluidic cartridges are described in further details below. The interior of the detector assembly comprises means for keeping the microfluidic cartridge in a fixed position when the cartridge is inserted into the slot.

Thus, when a microfluidic cartridge comprising a sample of interest is inserted into the slot 4 of the detector assembly 1, the detector assembly may perform measurements on the sample. The measurements may e.g. be optical measurements such photometric or colorometric measurement. It may also be measurements based on a charge-coupled device or magnetic measurements.

Figure 2:
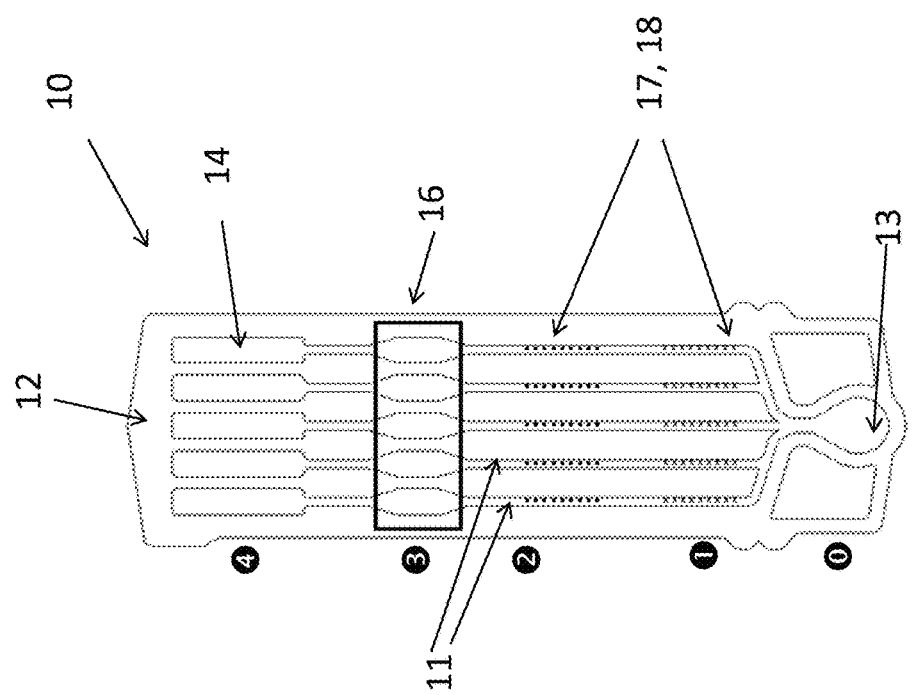
FIG. 2 shows a microfluidic cartridge according to the invention.

FIG. 2 shows a microfluidic cartridge 10 suitable for use in the invention. In this embodiment, the microfluidic cartridge 10 comprises a substrate 12 with five cavities in the form of channels 11. Each channel 11 comprises an inlet 13 and a sink 14 with a not shown flexible wall section.

The microfluidic cartridge 10 also comprises an indent which provides a read out section 16 for the channels 11, where the channels comprise a transparent window and where magnetic particles may be temporally immobilized using a not shown magnet.

In this embodiment each channel 11 comprises temporally immobilized magnetic particles and temporally immobilized fluorophores. The microfluidic device is divided into zones comprising zone 0 which is the inlet zone, zone 1 and zone 2 which comprise temporally immobilized fluorophores and magnetic particles 17 arranged such that they do not react until they are in contact with the liquid sample, zone 3 which is the read out zone and zone 4 which is the sink zone.

In an embodiment zone 1 comprises temporally immobilized fluorophores and zone 2 comprises temporally immobilized magnetic particles.

In an embodiment zone 1 comprises temporally immobilized magnetic particles and zone 2 comprises temporally immobilized fluorophores.

The microfluidic cartridge 10 may comprise several subzones of zone 1 and zone 2, if desired.

In use a liquid sample is fed to the inlet 13, the sample is sucked into zone 1 of the channels using the flexible wall section, which will later be described in more details. Optionally the liquid sample is pulsated in zone 1 to dissolve or re-suspend the immobilized elements 17 in zone 1. Thereafter the liquid sample is drawn further into the channels 11 to zone 2 for dissolving or re-suspending the immobilized elements 17 in zone 2. After a preselected incubation time the liquid sample is drawn fully into the sinks 14. The magnetic particles are immobilized in the read out zone 3. Moreover, if desired, the liquid sample can be reintroduced into the channels 11 by using the flexible wall of the sink 14 and the immobilized magnetic particles can be flushed using the liquid sample to remove not immobilized fluorophores and other elements that could potentially provide noise.

Figure 3:
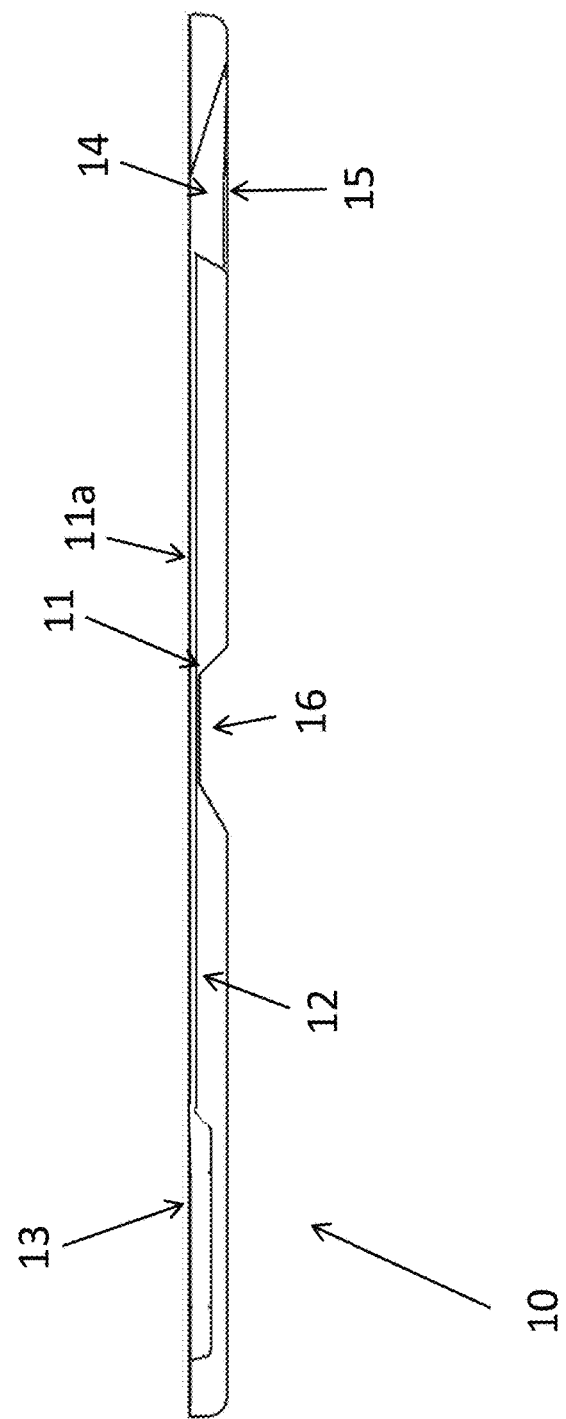
FIG. 3 shows the microfluidic cartridge in a side view.

FIG. 3 shows the microfluidic cartridge 10 of FIG. 1 seen from the side. Although known microfluidic cartridges in principle could be applied in the present invention, the micro fluidic cartridge shown is particularly designed for the purpose and provides additional benefits to the present invention as described herein.

The microfluidic cartridge 10 comprises a substrate 12 with five cavities in the form of channels 11. The channels 11 are provided in the form of grooves covered with a foil 11a. Each channel 11 is connected with an inlet 13 and at their opposite end the channels 11 are connected with a common sink 14. The inlet 13 has the shape of a well.

By pressing the flexible wall section 15 of the sink 14, the wall will be moved and air will be pressed out of the channels 11, and when the pressure is released the flexible wall section 15 will return to its initial position and a liquid sample arranged in the inlet 13 will be sucked into the channel 11 to a desired position. By further manipulating the flexible wall section the liquid sample can be drawn further into the channels 11 or it may be pulsated in the channels. Finally the flexible wall section 15 may be manipulated to collect the sample in the sink and to re-flush the sample into the channels, if desired. The flexible wall section 15 thereby provides a simple and cheap method of controlling a liquid sample in the micro fluidic device.

The micro fluidic cartridge also comprises an indent which provides a read out section 16 for the channels 11. In the read out sections 16 of the channels 11, the channels comprise a transparent window and the magnetic particles can be temporally immobilized using a not shown magnet. The magnet is mounted in the detector assembly which also includes a reading for reading signals through the read section 16.

Figure 4:
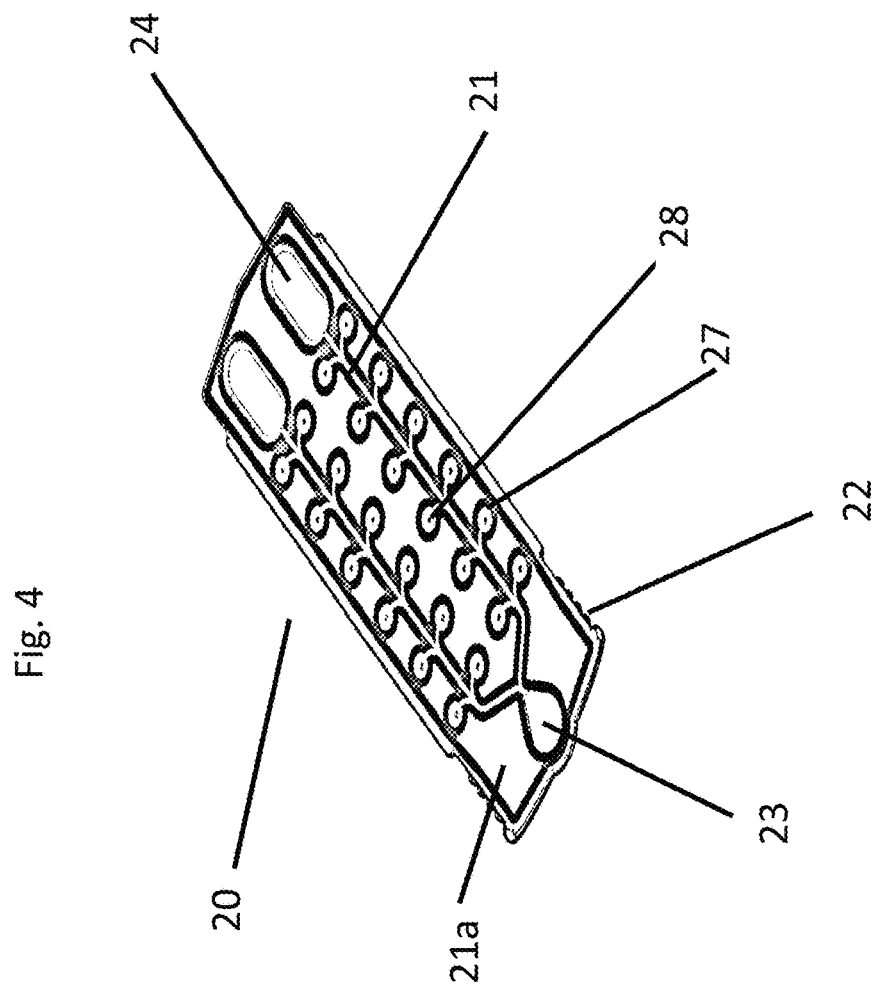
FIG. 4 shows an alternative embodiment of the microfluidic cartridge.
Figure 5:
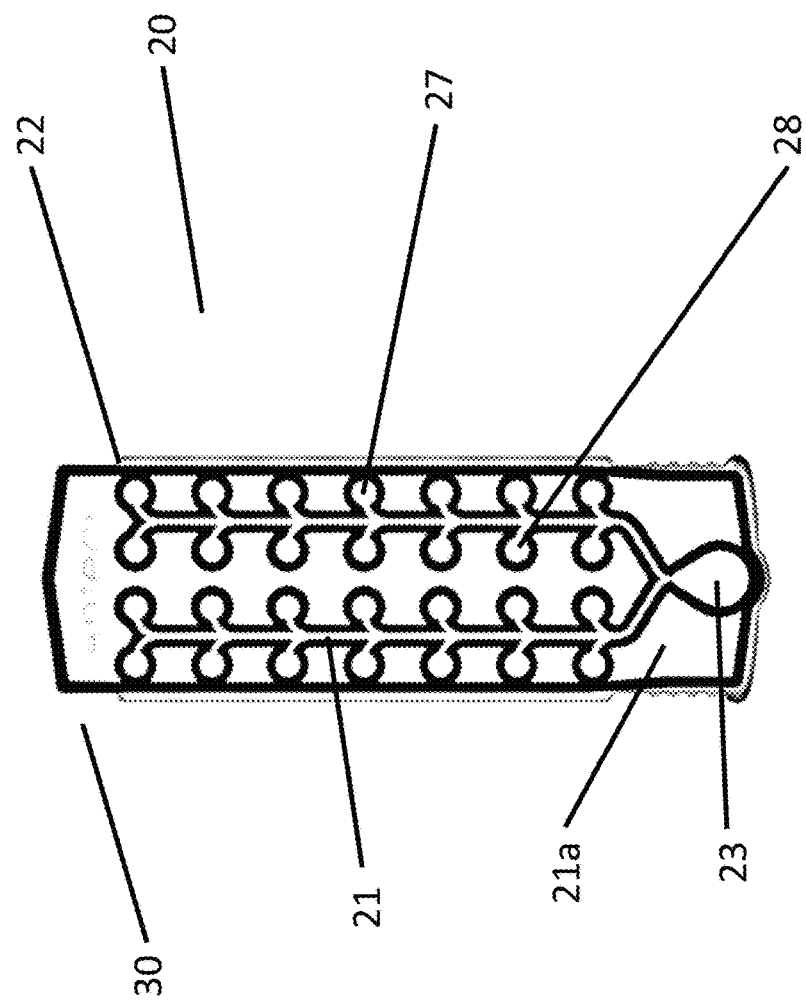
FIG. 5 shows yet another embodiment of the microfluidic cartridge.

FIGS. 4 and 5 show alternative embodiments of the microfluidic cartridge 20.

In FIG. 4 the microfluidic cartridge 20 is seen with two channels 21, which in one end is connected with an inlet 23 and in the opposite end connected with sinks 24.

Along the two channels 21 a number of chambers 27, 28 are located. Each chamber is connected with the channel and each chamber may comprise an analyte, which may react with a liquid sample which will fill the chambers when it passes from the inlet 23, through the channels 21 to the sink 24.

The channels 21, the inlet 23, the sinks 24, and the chambers 27, 28 are formed as recesses in the substrate 22. The access to the channels 21, the sinks 24, and the chambers 27, 28 are closed by a foil 21a, so they are only accessible via the inlet 23.

The chambers 27 and 28 are placed in pairs on each side of the channel 21. The chambers may comprise the same or different analytes. For example each pair along the channel may comprise the same analyte so the sample will be tested twice with same analyte, thereby improving the certainty of the measured results. Thus, the microfluidic cartridge 20 shown in FIG. 4 may e.g. be able to measure with twelve different analytes, i.e. the microfluidic cartridge 20 comprises twelve pairs of chambers 27, 28 located along the channels 21. The analytes may be a combination of analytes, which may be measured with different means, such as optical, electrical or magnetic means. Thus, the analytes may e.g. be immobilized magnetic particles or immobilized enzymes functioning as color-forming reactants, which will react with the liquid sample, when the sample enters the chamber.

FIG. 5 shows a microfluidic cartridge 20 which substantially corresponds to the microfluidic cartridge shown in FIG. 4. However, the sinks are omitted in this particular embodiment. When a liquid sample is placed in the inlet 23 it will flow into the channels 21 and the chambers 27 and 28 by means of pressure and capillary forces.

Consequently, the microfluidic cartridge comprises an inlet 23 connected with two channels 21, which are connected with pairs of chambers 27, 28 along the channels. The chambers 27 and 28 are transparent to light from a light source e.g. a multicolor-LED. As such the chambers 27 and 28 are suitable for use with optical detection means.

In the following FIGS. 6 to 9 the microfluidic cartridge illustrated in FIG. 5 is used as an example of some measurements which may be performed with the microfluidic detection system according to the invention.

Figure 6:
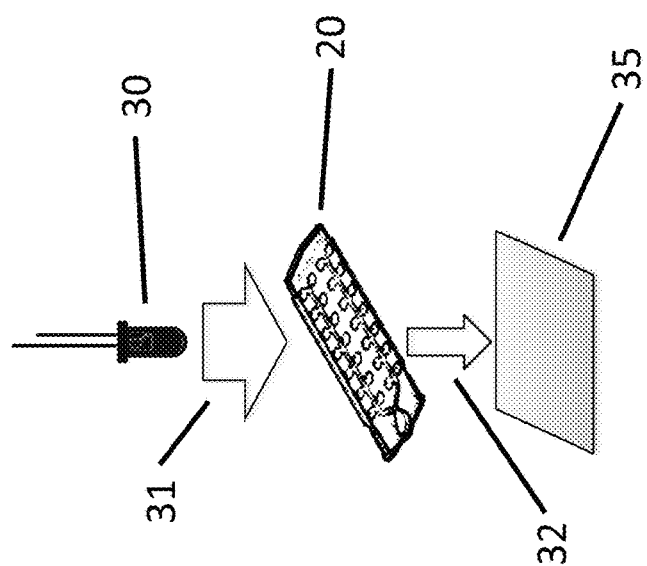
FIG. 6 shows detection with LED and CCD.

FIG. 6 shows an optical detection system in which an LED 30 emits a substantial monochromatic light beam towards a chamber in the microfluidic cartridge 20. The light beam bases the sample in the chamber and is transformed to a light beam 32 with different wavelength. The light beam 32 is detected by the CCD detector 35 below the microfluidic cartridge 20.

Figure 7:
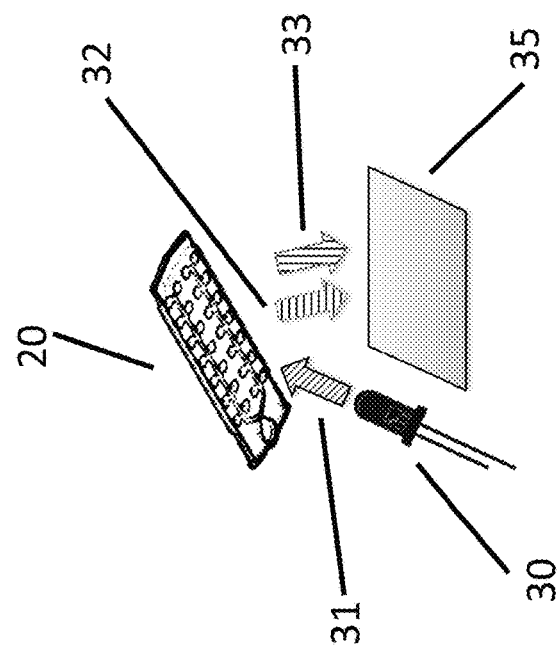
FIG. 7 shows alternative detection with LED and CCD.

FIG. 7 shows another embodiment in which the microfluidic cartridge 20 receives a light beam 31 emitted from the LED 30. The light beam 31 is reflected by the sample in the chamber of the microfluidic cartridge. The reflected light is divided into light with two different wavelengths 32 and 33 which are detected by the CCD detector 35 placed on the same side of the microfluidic cartridge 20 as the LED 30.

Figure 8:
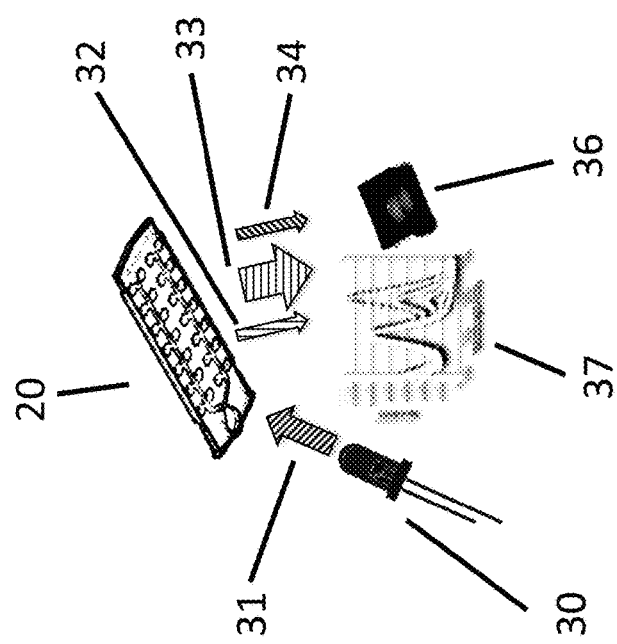
FIG. 8 shows detection with spectrometer.

FIG. 8 shows yet another embodiment of the detection system. In this embodiment the detection system utilizes a spectrometer 36 for detection of the light reflected from the sample in a chamber of the microfluidic cartridge 20. The light beam 31 is emitted from the LED 30 and reflected by the sample held in the microfluidic cartridge 20. The reflected light is reflected as light with three different wavelengths 32, 33 and 34. The reflected light is detected by the spectrometer 36 and the resulting curve is shown in the inserted box 37.

Figure 9:
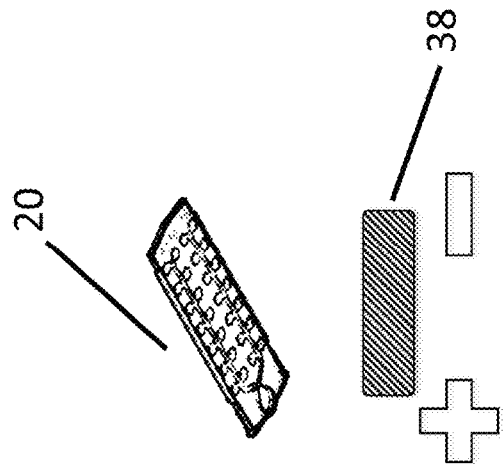
FIG. 9 shows electrical detection.

FIG. 9 illustrates an alternative embodiment of the detection system. This is a system where an array or electrodes 38 send a current through one or more of the chambers in the microfluidic cartridge 20. Due to the resistance in the sample, the detection system will be able to detect the nature of the sample.

FIG. 10 illustrates the principles of a light tunnel according to the invention. The light tunnel includes three LEDs 30a, 30b and 30 c, each emitting light with a wavelength which is different from the wavelengths of the other two LEDs. The LED 30a may emit light in the range: $610<\lambda<760$. The LED 30b may emit light in the range $570<\lambda<590$, and finally the LED 30c may emit light in the range: $450<\lambda<500$.

Each LED is intended to emit light to one or more specific detection sites, and to avoid transmission of incident light to detection sites where it is not desired, the light tunnel is constructed with partition members 39 which will ensure that undesired transmission of incident light is avoided.

Thus, each LED 30a, 30b and 30c is enclosed by partitions members 39, which will ensure that the light emitted from the LED only transmits light to the detection site for which the light is intended.

The light tunnel makes it possible to transmit light through two or more detection sites simultaneously. As seen in the embodiment of FIG. 10, the LEDs 30a, 30b and 30c transmit light simultaneously through three different detection sites on the microfluidic cartridge 20. The resulting light beams are detected by the CCD detector 35.

Figure 11:
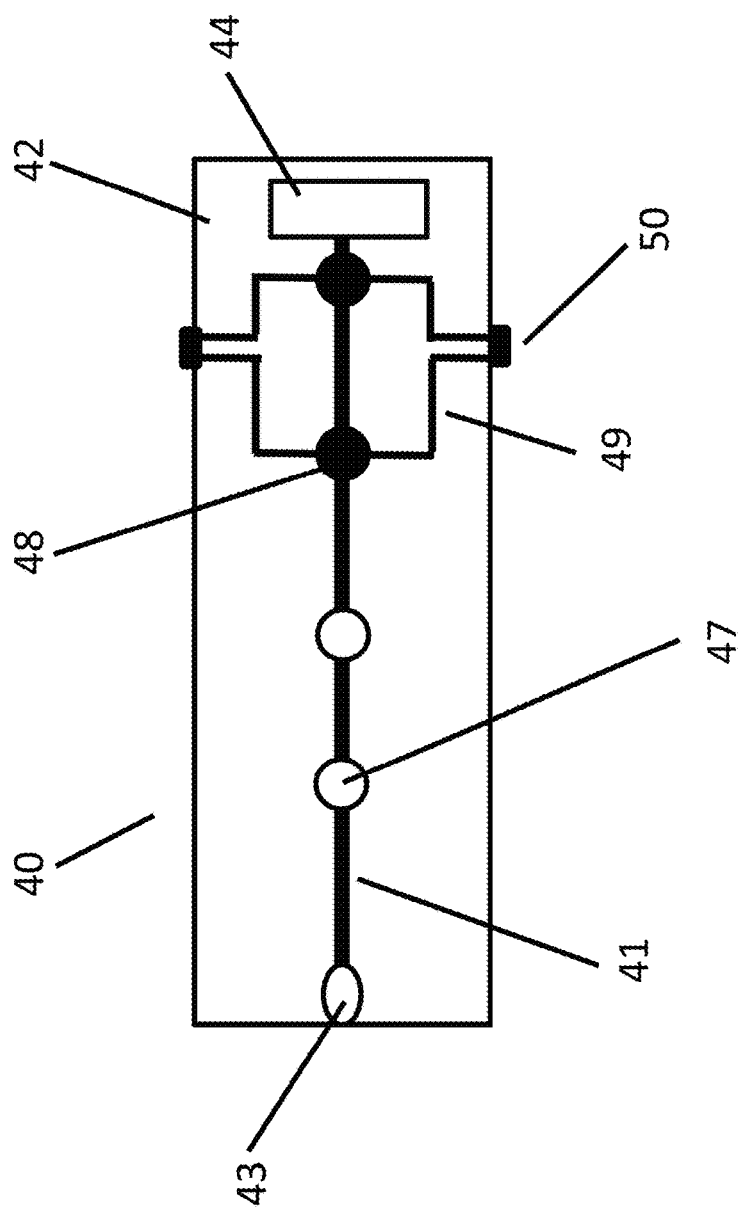
FIG. 11 shows a microfluidic cartridge adapted for electrical detection.

FIG. 11 shows an alternative embodiment of a microfluidic cartridge 40 according to the invention. The microfluidic cartridge 40 comprises an inlet 43 for introduction of a sample. The inlet 43 is connected with a channel 41 which in the opposite end is connected with a sink 44. Along the length of the channel 41 are located two detection sites 47 for optical detection and further two detection sites 48 for electrical detection.

The electrical detection sites 48 may comprise electrodes which are connected with connection pads 50 by means of electrical wiring 49. The electrical wiring may be printed on the substrate 42 of the microfluidic cartridge 40.

The connection pads 50 may be connected with corresponding connection pads in the detection assembly and to an electrical reader, such as a voltmeter.

The figures only illustrate a limited number of embodiments according the invention, and the full scope of the invention is defined in the claims. However, it is clear that several combinations are possible and the optical detection may be combined with magnetic and/or electrical detection.

The invention claimed is:

1. A microfluidic detection system comprising a microfluidic cartridge and a detector assembly,
the microfluidic cartridge comprises a first and a second side and at least one flow channel and an inlet to the at least one flow channel for feeding a liquid sample, the at least one flow channel comprises a plurality of first optical detection sites, and
the detector assembly comprises a slot for inserting the microfluidic cartridge and a first fixed light source with a beam path and an optical reader for reading out optical signals from at least one of said first optical detection sites, said detector assembly and the microfluidic cartridge are constructed such that when the microfluidic cartridge is inserted to a first predetermined position into said slot, one of said first optical detection sites of the microfluidic cartridge is positioned in the beam path of the first light source, and when the cartridge is inserted to a second predetermined position into said slot, another one of the first optical detection sites of the microfluidic cartridge is positioned in the beam path of the first light source, wherein each of said first and said second predetermined positions of said microfluidic cartridge into said slot are determined by projecting flanges arranged on the microfluidic cartridge and cavities arranged on the detector assembly at selected positions or projecting flanges arranged on the detector assembly and cavities arranged on the microfluidic cartridge at the selected positions, which engage or snap into place to temporarily position the microfluidic cartridge in the detector assembly at one of the first and the second predetermined positions, said projecting flanges and cavities comprises a first set of projecting flanges and cavities which correspond to the first predetermined position and said projecting flanges and cavities comprises a second set of projecting flanges and cavities which correspond to the second predetermined position.

2. The microfluidic detection system of claim 1, wherein said first light source comprises a multicolor light emitting diode (LED) configured for emitting a plurality of different light beams having different wavelengths and a circuitry for switching said plurality of different light beams on and off.

3. The microfluidic detection system of claim 1, wherein the slot of the detector assembly and the microfluidic cartridge are constructed such that when said microfluidic cartridge is inserted to a predetermined position into said slot, one of the first optical detection sites of the microfluidic cartridge is positioned in the beam path of the first light source, the predetermined position of said microfluidic cartridge into said slot is determined by a click arrangement holding the microfluidic cartridge in a temporally fixed position.

4. The microfluidic detection system of claim 1, wherein the optical reader is arranged for reading out at least one of an absorption property, a reflection property or an emitting property from a liquid sample in at least one of said first detection sites when said cartridge is inserted into said slot of said detector assembly.

5. The microfluidic detection system of claim 1, wherein the optical reader is a digital imaging reader.

6. The microfluidic detection system of claim 1, wherein the optical reader comprises a charge-coupled device (CCD) reader.

7. The microfluidic detection system of claim 1, wherein the circuitry of said first light source is configured for switching said plurality of different light beams on and off independently of each other.

8. The microfluidic detection system of claim 1, wherein the detector assembly is programmed to switch the plurality of different light beams on and off such that only one of the different light beams is switched on at a time.

9. The microfluidic detection system of claim 1, wherein the plurality of different light beams comprise from 2 to 5 different light beams.

10. The microfluidic detection system of claim 1, wherein each of the plurality of different light beams independently of each other have a spectral width of up to about 50 nm.

11. The microfluidic detection system of claim 1, wherein said plurality of different light beams of said multicolor-LED are monochromatic light beams.

12. The microfluidic detection system of claim 1, wherein said plurality of different light beams of said multicolor-LED comprise at least one of a light beam having a center wavelength of about 575 nm to about 625 nm or a light beam having a center wavelength of about 425 nm to about 475 nm.

13. The microfluidic detection system of claim 1, wherein said plurality of different light beams of said multicolor-LED comprise at least three monochromatic light beams selected from red, orange, yellow, green or blue light beams.

14. The microfluidic detection system of claim 1, wherein said at least one flow channel of said microfluidic cartridge comprises a plurality of additional optical detection sites, and the detector assembly comprises at a plurality of additional fixed light source with respective beam paths, the slot of the detector is shaped such that when said microfluidic cartridge is inserted into said slot, the plurality of additional optical detection sites of the microfluidic cartridge are positioned in respective beam paths of the plurality of additional light sources, each of said plurality of additional light sources comprises a multicolor light emitting diode (LED) configured for emitting a plurality of different light beams having different wavelengths and a circuitry for switching said plurality of different light beams on and off, said optical reader is configured for reading out optical signals from said additional optical detection sites and said detector assembly comprises at least one additional optical reader configured for reading out optical signals from said additional optical detection sites.

15. The microfluidic detection system of claim 1, wherein said detector assembly comprises a light tunnel for one or more of the fixed light sources to prevent the beams from the respective fixed light sources to transmit light to two or more detection sites simultaneously.

16. The microfluidic detection system of claim 1, wherein said at least one flow channel of said microfluidic cartridge comprises a plurality of detection cites for performing a plurality of different assays.

17. The microfluidic detection system of claim 16, wherein the plurality of detection sites comprise at least one electrical detection site, said electrical detection site comprises electrodes arranged for performing an electrochemical detection at the electrical detection site, said electrodes comprise electrical wires connected to microfluidic cartridge connection pads, the detector assembly comprises at least one electrical reader for reading out electrical signals out from the electrical detection sites.

18. The microfluidic detection system of claim 17, wherein the electrical reader comprises a voltmeter electrically connected to voltmeter connection pads arranged in the slit such that the microfluidic cartridge connection pads are in electrical connection with said voltmeter connection pads when said microfluidic cartridge is inserted into said slot.

19. The microfluidic detection system of claim 1, wherein said detector assembly comprises at least one output interface and a processor, said microfluidic cartridge comprises a machine readable code comprising instructions about assays to be performed using the cartridge and said detector assembly comprises a code reader for reading the machine readable code and feeding the instructions about the assays to be performed to the processor, wherein the processor is programmed to control at least one of the readers and the output interface at least partly based on instructions obtained from the machine readable code, preferably said at least one reader is at least one of the optical reader and the electrical reader.

* * * * *